(12) United States Patent
Baldwin et al.

(10) Patent No.: US 7,207,993 B1
(45) Date of Patent: Apr. 24, 2007

(54) APPARATUS AND METHOD FOR REPAIRING THE FEMUR

(75) Inventors: Eric A. Baldwin, Ishpeming Township, MI (US); Thomas S. Kilpela, Marquette, MI (US); Burns O. Severson, Marquette, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 09/775,891

(22) Filed: Feb. 2, 2001

Related U.S. Application Data

(60) Provisional application No. 60/179,999, filed on Feb. 3, 2000.

(51) Int. Cl.
*A61B 17/58* (2006.01)

(52) U.S. Cl. .............. 606/70; 606/60; 606/69; 606/65

(58) Field of Classification Search .......... 606/60, 606/69, 70, 71, 72, 74, 75, 65
See application file for complete search history.

(56) References Cited

U.S. PATENT DOCUMENTS

| | | | |
|---|---|---|---|
| 3,824,995 A | 7/1974 | Getscher et al. | |
| 3,939,498 A | 2/1976 | Lee et al. | |
| 4,120,298 A | 10/1978 | Fixel | |
| 4,153,953 A | 5/1979 | Grobbelaar | |
| 4,163,292 A | 8/1979 | Averett, Jr. | |
| 4,269,180 A | 5/1981 | Dall et al. | |
| 4,465,065 A * | 8/1984 | Gotfried | 606/65 |
| 4,473,068 A | 9/1984 | Oh | |
| 4,651,724 A * | 3/1987 | Berentey et al. | 606/69 |
| 4,875,474 A | 10/1989 | Border | |
| 4,889,110 A | 12/1989 | Galline et al. | |
| 4,988,350 A | 1/1991 | Herzberg | |
| 5,015,248 A * | 5/1991 | Burstein et al. | 606/74 |
| 5,324,291 A | 6/1994 | Ries et al. | |
| 5,342,366 A | 8/1994 | Whiteside et al. | |
| 5,382,251 A | 1/1995 | Hood et al. | |
| 5,415,658 A | 5/1995 | Kilpela et al. | |

(Continued)

FOREIGN PATENT DOCUMENTS

| | | |
|---|---|---|
| WO | WO89/06940 | 8/1989 |

(Continued)

*Primary Examiner*—Henry Bennett
*Assistant Examiner*—Dinnatia Doster-Greene
(74) *Attorney, Agent, or Firm*—FItch, Even, Tabin & Flannery

(57) ABSTRACT

A method and apparatus for repairing the femur. A connector is provided having a claw-like member to engage with the greater trochanter. Along the body of the connector are a plurality of cable apertures and cable screws to receive and engage with cables that loop around the femur. Along the inferior end of the connector are bone screw slots and bone screws engaging the connector with the femur. The bone screws provide added support to the re-attached greater trochanter and provide support for periprosthetic fractures. The connector may be used to re-attach the greater trochanter by impacting a connector onto the greater trochanter, positioning the greater trochanter onto the femur, passing cables around the femur and through the connector, tensioning the cables to provide engagement between the greater trochanter and the femur, and attaching the connector to the femur using at least one bone screw.

11 Claims, 15 Drawing Sheets

U.S. PATENT DOCUMENTS

| | | |
|---|---|---|
| 5,456,686 A | 10/1995 | Klapper et al. |
| 5,462,547 A | 10/1995 | Weigum |
| 5,468,242 A | 11/1995 | Reisberg |
| 5,591,168 A * | 1/1997 | Judet et al. .................. 606/65 |
| 5,607,430 A | 3/1997 | Bailey |
| 5,665,089 A * | 9/1997 | Dall et al. .................. 606/71 |
| 5,702,399 A * | 12/1997 | Kilpela et al. ............... 606/72 |
| 5,702,656 A | 12/1997 | Sarver et al. |
| 5,741,259 A * | 4/1998 | Chan ......................... 606/74 |
| 5,741,266 A | 4/1998 | Moran et al. |
| 5,766,218 A * | 6/1998 | Arnott ....................... 606/151 |
| 5,792,143 A | 8/1998 | Samuelson et al. |
| 5,797,916 A * | 8/1998 | McDowell .................. 606/74 |
| 5,810,821 A | 9/1998 | Vandewalle |
| 5,860,969 A | 1/1999 | White et al. |
| 5,868,746 A | 2/1999 | Sarver et al. |
| 5,885,295 A | 3/1999 | McDaniel et al. |
| 5,895,390 A | 4/1999 | Moran et al. |
| 5,935,127 A | 8/1999 | Border |
| 5,941,881 A | 8/1999 | Barnes |
| 5,993,449 A * | 11/1999 | Schlapfer et al. ............ 606/60 |
| 5,993,452 A | 11/1999 | Vandewalle |
| 6,022,352 A | 2/2000 | Vandewalle |
| 6,066,141 A * | 5/2000 | Dall et al. ................... 606/74 |
| 6,183,474 B1 * | 2/2001 | Bramlet et al. .............. 606/66 |
| 6,338,734 B1 * | 1/2002 | Burke et al. ................. 355/53 |
| 6,508,819 B1 * | 1/2003 | Orbay ........................ 606/69 |

FOREIGN PATENT DOCUMENTS

| | | |
|---|---|---|
| WO | WO89/07056 | 8/1989 |
| WO | WO94/16645 | 8/1994 |
| WO | WO94/16951 | 8/1994 |
| WO | WO95/15129 | 6/1995 |
| WO | WO95/16399 | 6/1995 |
| WO | WO95/26687 | 10/1995 |
| WO | WO96/11784 | 4/1996 |
| WO | WO97/29787 | 8/1997 |
| WO | WO00/03855 | 1/2000 |
| WO | WO00/23012 | 4/2000 |

* cited by examiner

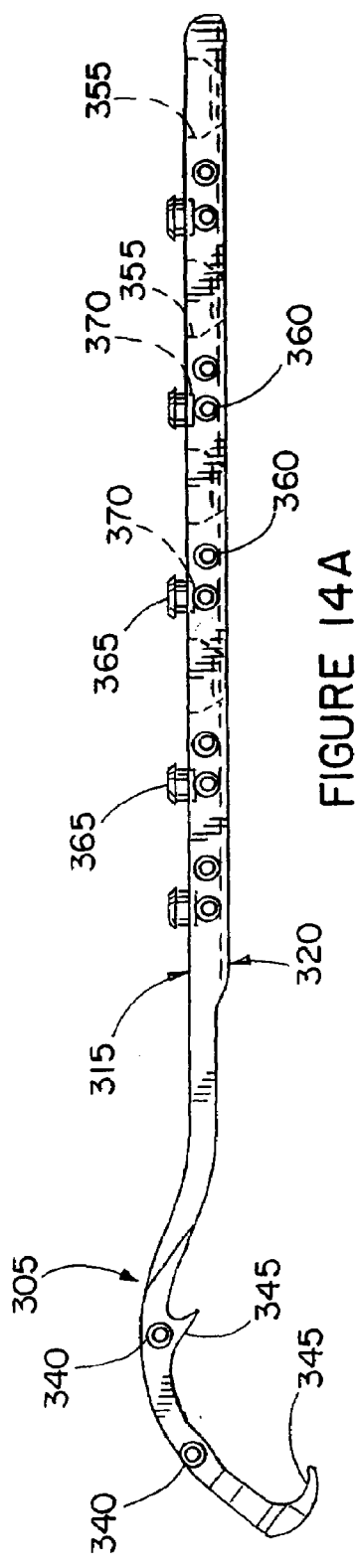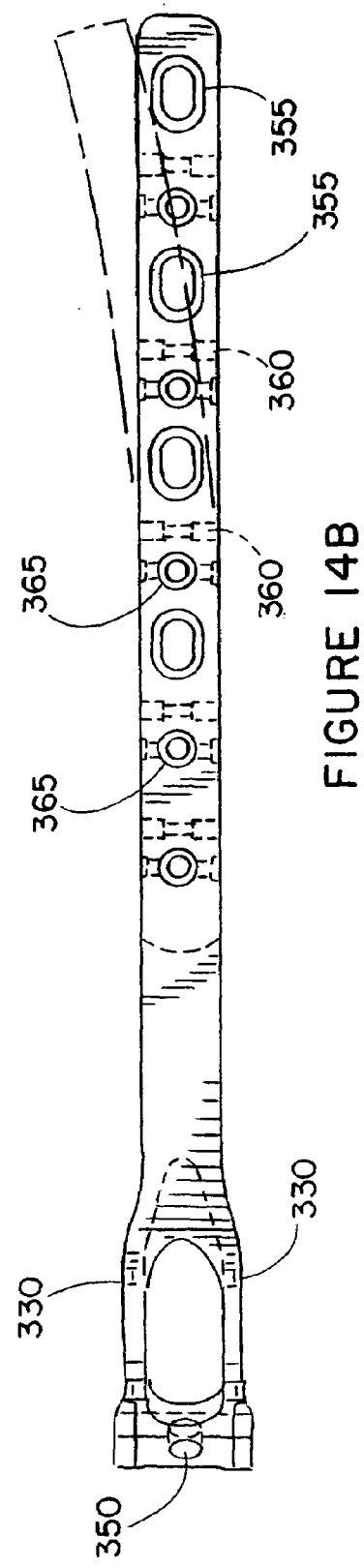
FIGURE 14A
FIGURE 14B

APPARATUS AND METHOD FOR REPAIRING THE FEMUR

This is a non-provisional application of Provisional Application Ser. No. 60/179,999 filed on Feb. 3, 2000 for which priority is claimed. This provisional application is incorporated herewith by reference.

BACKGROUND OF THE INVENTION

1. Field of the Invention

The invention relates generally to surgical methods and apparatus for the repair of the femur and more particularly related to methods and apparatus for repairing periprosthetic fractures and/or re-attaching the greater trochanter to the femur.

2. Description of the Prior Art

The bone structure of the hip joint often requires orthopedic surgery. Total hip replacements are performed most commonly because of progressively severe arthritis in the hip joint. The most common type of arthritis leading to total hip replacement is degenerative arthritis (osteoarthritis) of the hip joint. Other conditions leading to total hip replacement include bony fractures of the hip joint, and death (necrosis) of the femur. The progressively intense chronic pain together with impairment of daily function including walking, climbing stairs and even rising from a sitting position, eventually become reasons to consider a total hip replacement.

A total hip replacement is a surgical procedure whereby the diseased cartilage and bone of the hip joint is surgically replaced with artificial materials. As shown in FIG. 1, the normal hip joint is a ball and socket joint. The socket is a "cup-shaped" bone of the pelvis 180 called the acetabulum. The ball is at the head of the femur 170. Total hip joint replacement generally involves: (1) surgically removing the diseased ball and socket; and (2) replacing them with a metal ball and stem 210 inserted into the femur bone and an artificial plastic cup socket 220 (see FIG. 2). The metallic artificial ball and stem are referred to as the "prosthesis." Upon inserting the prosthesis into the central core of the femur, it is fixed with a bony cement. Alternatively, a "cement-less" prosthesis may be used that allows bony in growth from the normal femur into the prosthesis stem. Even after hip replacement surgery, it often becomes necessary to perform further surgery due to further deterioration of the bone or to perform further repair of the replaced hip. If a patient falls and injures a replaced hip, the bone fracture will often occur at the distal tip of the prothesis, thereby requiring replacement of the prosthesis and/or repair of the femur.

Presently, a number of orthopedic surgical techniques exist for replacing or repairing the hip joint. A number of these total hip procedures require osteotomizing or removing the greater trochanter (illustrated by line 205 in FIG. 2). Removal of this portion of the femur provides the surgeon with access to the stem of the prosthesis to conduct the necessary hip replacement procedure. After the necessary hip replacement procedure, the greater trochanter must then be re-attached to the femur.

A few tools exist to enable re-attachment of the greater trochanter to the femur. One known technique utilizes a cable implant to hold bone portions together. Cables and/or wires secure the bones and the bone fragments in place. Typically, surgical cables are implanted using tensioning devices, which apply tension to a cable looped around the bone. Crimps are then added and deformed to clamp the cable loop in place. One example of such techniques is disclosed in U.S. Pat. No. 5,415,658, the entire writing of which is incorporated herein by reference. Another such example is the CABLE-READY brand cable grip system sold by Zimmer of Warsaw, Ind.

These techniques, however, rely entirely on cables to ensure that the device is securely fastened to the bone or bone fragments. Accordingly, it is desirable to provide a technique to re-attach the greater trochanter to the femur that provides an additional level of stability to the fracture site.

It is also desirable to provide a technique to repair periprosthetic fractures. Peri-prosthetic fractures have become increasingly common as more patients undergo total hip replacement, and may occur intraoperatively or at some time after surgery. The patient must then have an additional surgical procedure to repair the fracture.

It is further desirable to provide a device that can be fitted to femoral heads and femoral shafts of a variety of sizes and shapes without need for manufacture and inventory of an unreasonable number of differently sized models of the apparatus.

SUMMARY OF THE INVENTION

The aforementioned problems are addressed by the present invention, which in a preferred embodiment, provides a connector for repairing a femur including techniques for repairing periprosthetic fractures and/or re-attaching the greater trochanter to the femur. The connector includes a claw-like member to engage with the greater trochanter. Along the body of the connector as well as along the superior end are a plurality of cable apertures and cable screws to receive and engage with cables that loop around the femur. Along the inferior end of the connector is at least one bone screw slot and bone screw engaging the connector with the femur. The bone screw provides torsional stability and provides a means for stabilizing bony fragments for periprosthetic fractures.

As preferred, the connector may be bowed or rotated at the inferior end to more properly align itself with the femur. Also to achieve this purpose, the connector may include a transition portion that allows the surgeon to bend the connector. Also included in the connector is a driver slot along the superior portion to allow the surgeon to place the connector to the greater trochanter.

The present invention also includes a method for repairing periprosthetic fractures and/or re-attaching the greater trochanter to the femur involving the steps of impacting a connector onto the greater trochanter, re-positioning the greater trochanter onto the femur, passing cables around the femur and through the connector, tensioning the cables to provide engagement between the greater trochanter and the femur, and attaching the connector to the femur by securing the cables with the cable screws and using at least one bone screw.

The invention may also include a modular feature that allows the apparatus to be assembled using a superior end and an inferior end of choice size to closely fit the patient's skeletal frame. In the preferred embodiment, the superior connector includes a first transitional portion that mates with a second transitional portion of the inferior portion. The two portions may be secured together using one or more screws. It is clear, however, that one skilled in the art would be able to utilize a variety of methods for securing the two portions together.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 13–17 are diagrams of additional embodiments of a connector for re-attaching a greater trochanter to the femur in accordance with a preferred embodiment of the present invention.

DETAILED DESCRIPTION OF THE PREFERRED EMBODIMENT

Figure 1:
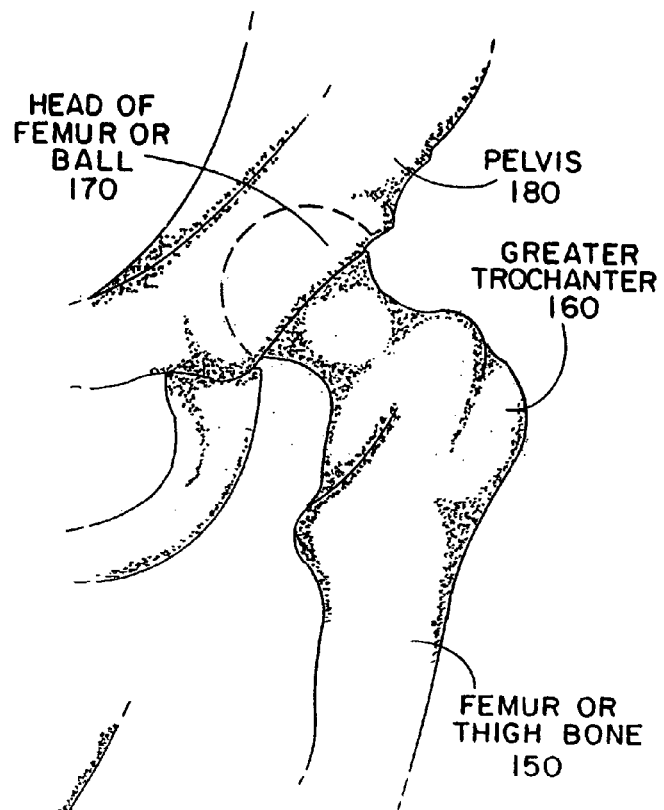
FIG. 1 is a diagram of the femur and pelvis.
Figure 2:
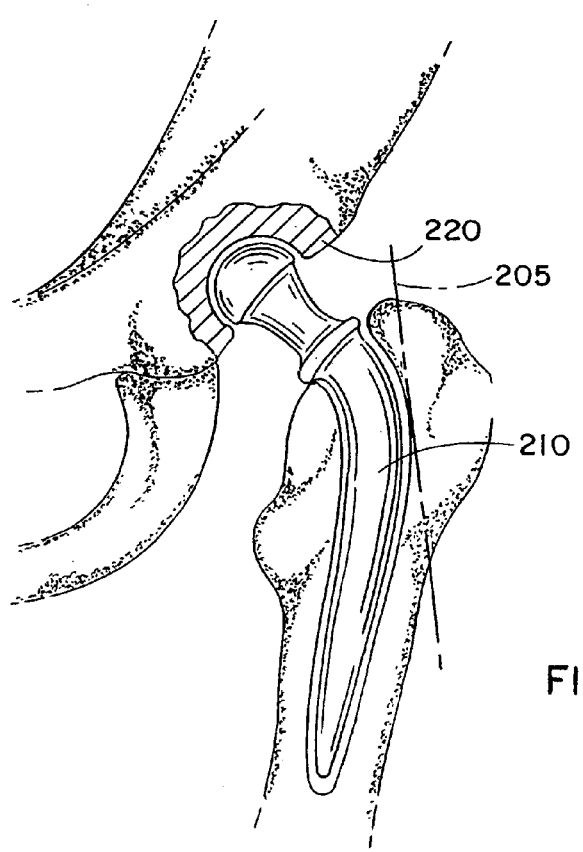
FIG. 2 is a diagram of the replaced femoral head and pelvis.
Figure 3:
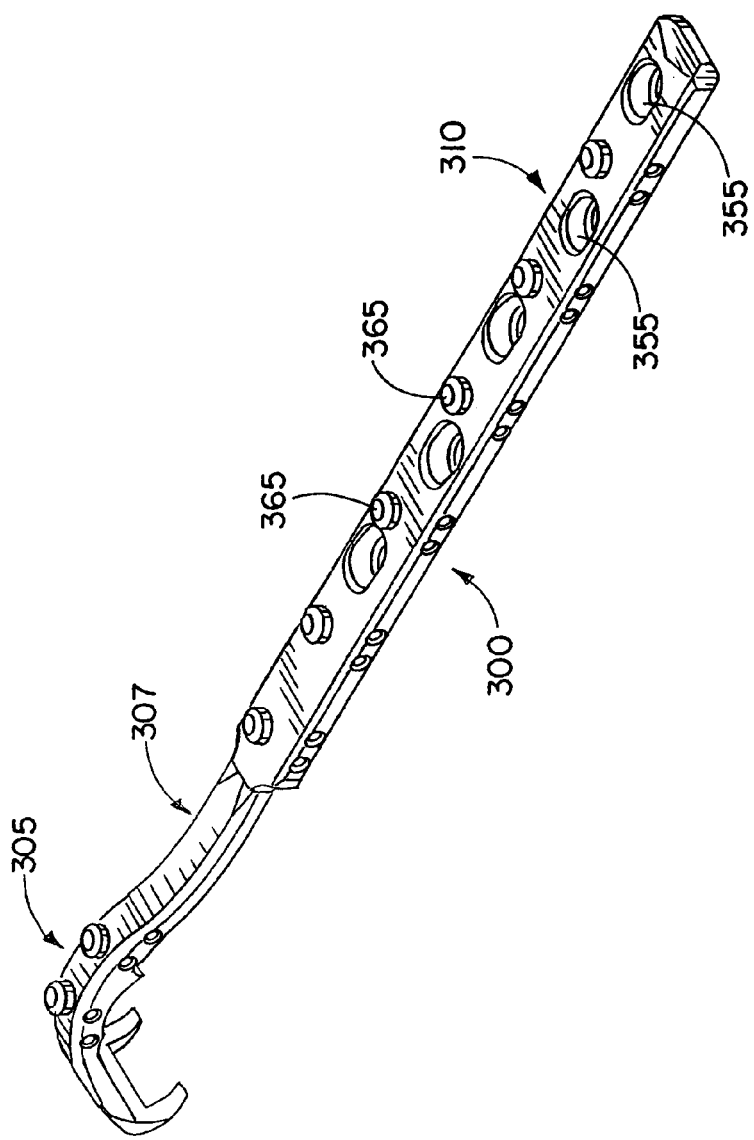
FIG. 3 is a perspective view of an exemplary connector for repairing a femoral periprosthetic fracture and/or re-attaching the greater trochanter to the femur in accordance with a preferred embodiment of the present invention.
Figure 4:
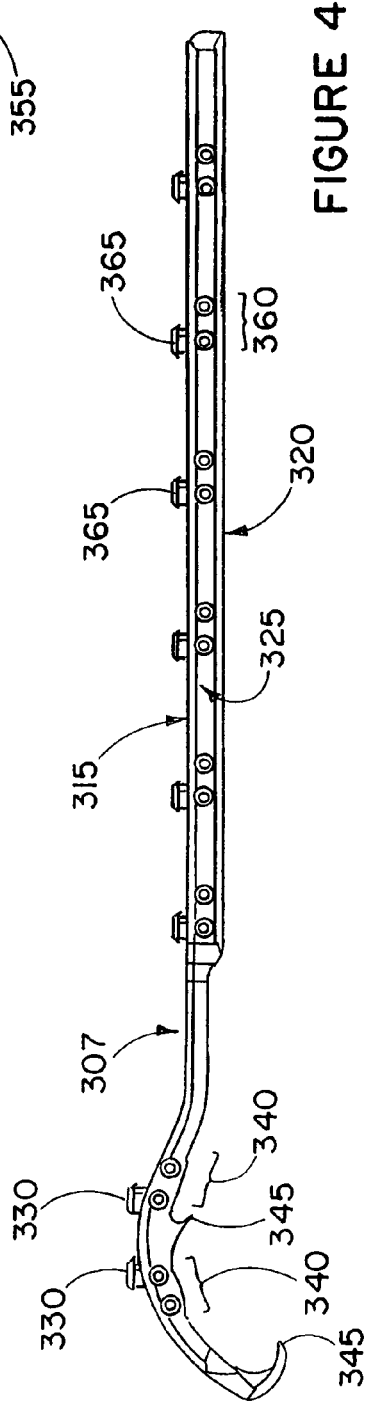
FIG. 4 an anterior/posterior view of the connector of FIG. 3.
Figure 5A:
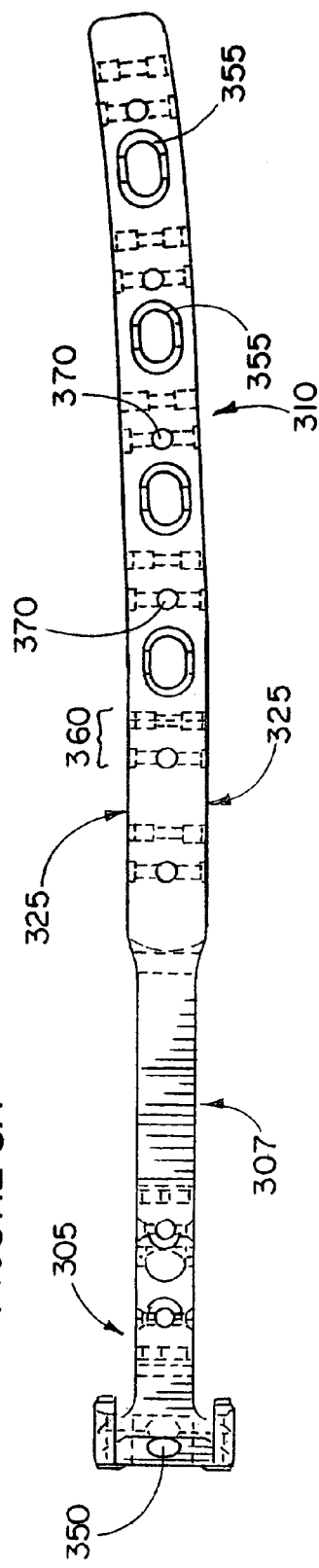
FIGS. 5A and 5B are lateral and anterior/posterior views, respectively, of another embodiment of a connector.
Figure 5B:
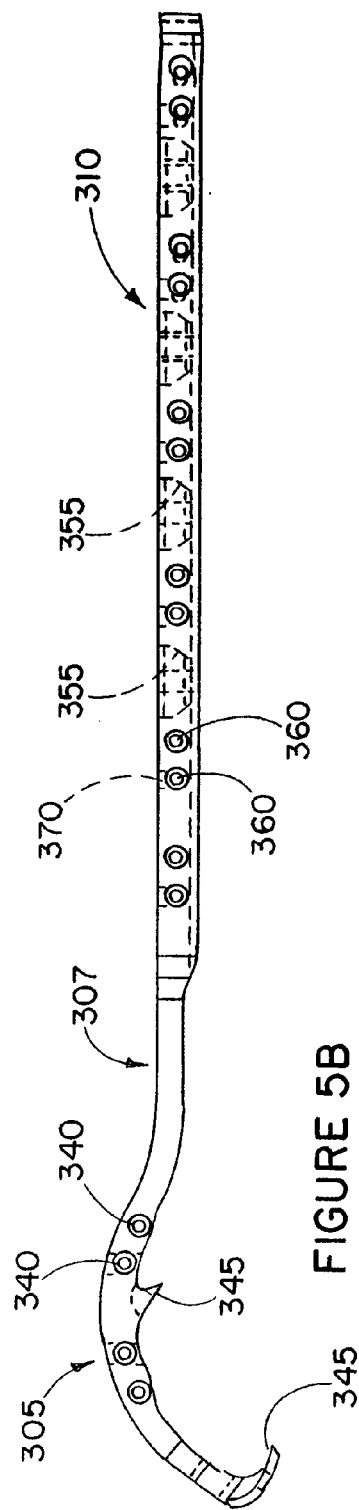

FIGS. 3–5 illustrate an exemplary connector 300 for re-attaching a greater trochanter 160 to the femur 150 in accordance with a preferred embodiment of the present invention. Connector 300 generally has a superior end 305, an inferior end 310, a transition portion 307, a lateral side 315, a medial side 320, and opposing anterior and posterior sides 325. Connector 300 may be of an implant grade material, preferably titanium or stainless steel, or of a bio-absorbable material.

The superior end 305 of the connector 300 has an improved anatomically-designed bow that fits and cradles the greater trochanter 160. In particular, the superior end 305 includes one or more cable apertures or grooves 340, and one or more claws or claw-like members 345. Claws 345 include extensions or hooks to allow the superior end to better grasp onto the greater trochanter 160. The cable apertures 340 serve to attach and fixate the connector 300 to the greater trochanter 160 in accordance with the present invention. The apertures 340 may be perpendicular to the sides 325 of the connector 300 (as shown in the figures), they may be angled to provide a cable path that reduces the stress on the cable, and/or they may have a curved path to help direct the cable in a stress relieving direction. The cables extending through the apertures 340 may be crimped. In this regard, crimping may be external or the superior end 305 may have integral crimps 330 attached thereto. The superior end 305 includes a driver slot 350 for engaging with a driver (not shown). As defined herein, apertures 340 may include surface grooves to route the cable over the connector 300.

The transition portion 307 of the connector 300 is preferably sufficiently narrow such that it may be bent by a surgeon to provide a better fit between the connector 300 and the femur 150. Optionally, as shown in FIG. 5A, the inferior end 310 of the connector 300 may be bowed to conform with the anterior bow in the femur 150. The inferior end 310 may also be bowed in other directions to follow any other unique bows or rotations of the femur 150.

The inferior end 310 of the connector 300 includes one or more bone screw slots 355 to receive a bone screw (not shown). The slots 355 include threaded holes and are preferably evenly spaced along the length of the inferior end 310, although any spacing geometry may be used and still be considered within the scope of the present invention. As illustrated in FIGS. 3–5, five slots 355, roughly one inch apart, are provided, however, those skilled in the art will appreciate that connector 300 may include any number of slots 355 to be considered within the scope of the present invention. As preferred, the range is between two and five slots 355. Slots 355 may be standard slots or may be compression slots. Compression slots are generally known in the art. Further, slots 355 may be of differing geometries. Advantageously, as shown herein, slots 355 allow bone screws to be inserted into the femur 150 to provide a more durable connection, to provide torsional stability, to provide stability for bony fragments of periprosthetic fractures, and to provide more support for the greater trochanter 160 while it heals. Bone screws cause connector 300 to create a force to push the greater trochanter 160 toward the femur 150. Further, slot 355 may be configured such that bone screws may be easily angled past the prosthesis, thereby avoiding the prosthesis when the bone screw is inserted. Bone screws may be unicortical or bicortical screws.

Inferior end 310 also includes one or more pairs of cable apertures 360. Though not required, the cable apertures 360 are shown as being evenly spaced along the length of the inferior end 310 in an alternating fashion with the slots 355. One or more of the paired apertures includes a cable screw slot 370 for receiving a cable screw 365. The cable screw 365 may be wound into the slot 370 to affect the size of the cable aperture 360. The particulars of the cable mechanism are generally known in the art and are disclosed further in U.S. Pat. No. 5,415,658, the entire writing of which is incorporated herein by reference. Again, those skilled in the art will appreciate that any number of cable apertures 360 may be used to still be considered within the scope of the present invention.

FIGS. 13–17 disclose additional embodiments of connector for re-attaching a greater trochanter 160 to the femur 150 in accordance with a preferred embodiment of the present invention. As illustrated by these alternative embodiments, integral crimps may or may not be used for the cable apertures along the superior end of the connector. In addition, the number of slots 355, cable screws 365, and cable apertures 360 may varied.

Figure 6:
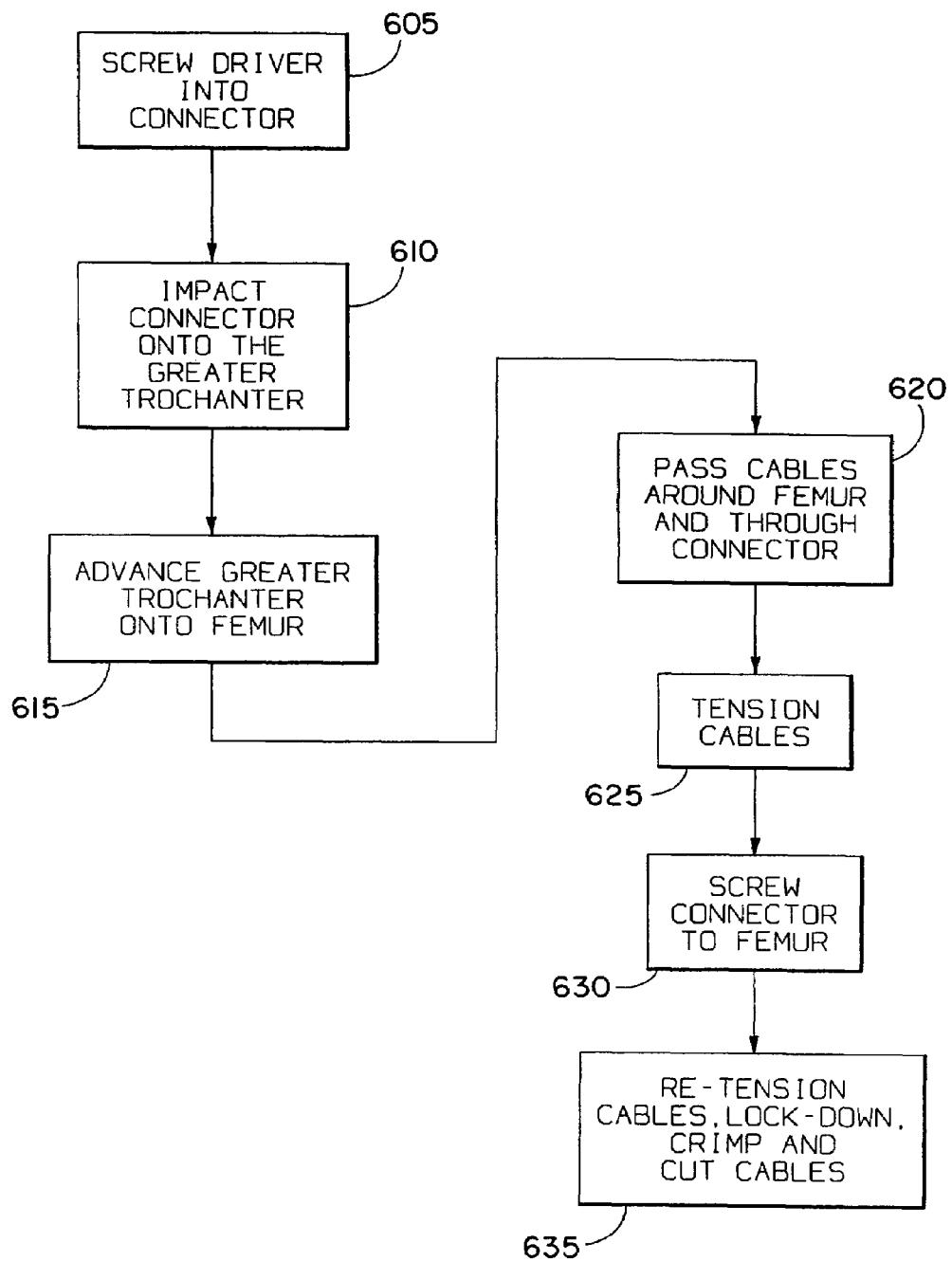
FIG. 6 is a flow chart illustrating the procedure for re-attaching a greater trochanter to the femur in accordance with a preferred embodiment of the present invention.
Figure 7:
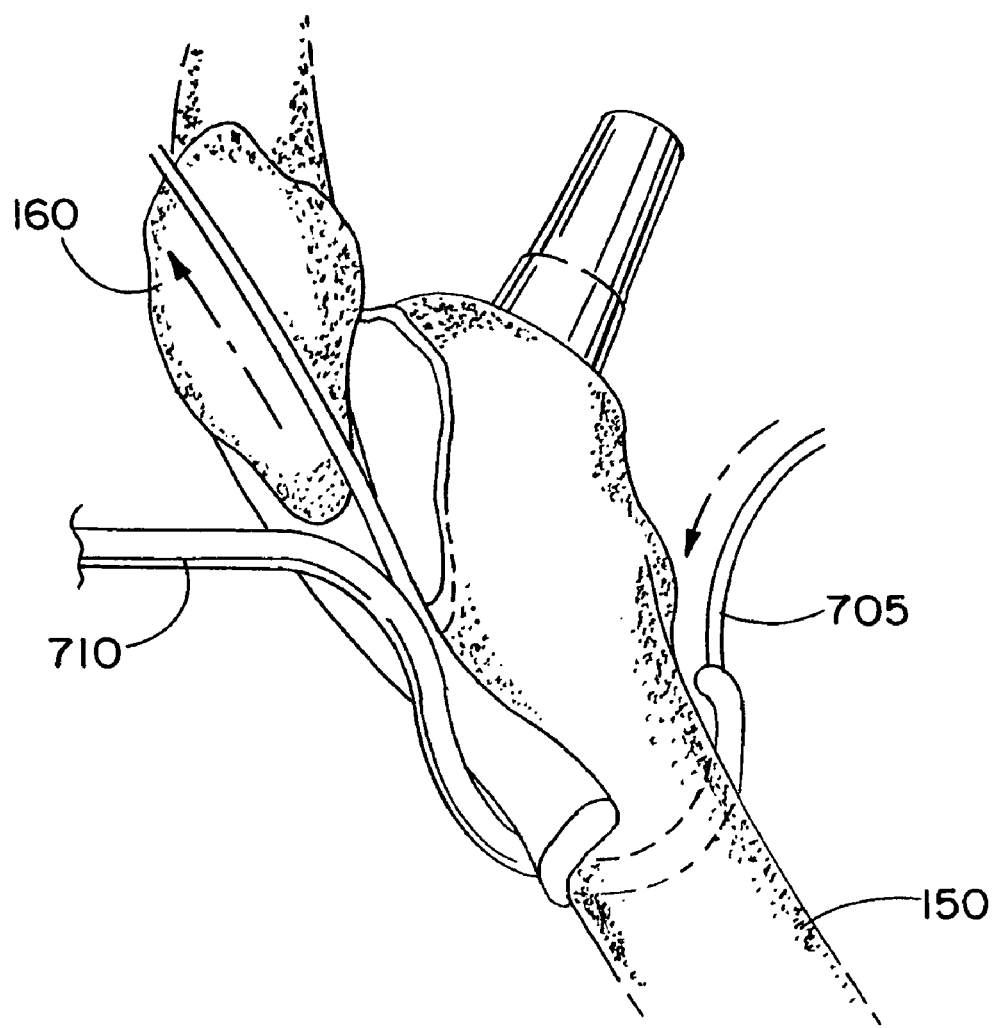
FIGS. 7–12 are diagrams of the surgical procedure for re-attaching the greater trochanter to the femur in accordance with the steps detailed in FIG. 6.

FIGS. 6–12 generally illustrate an exemplary procedure for re-attaching the greater trochanter 160 to the femur 150 in accordance with a preferred embodiment of the present invention. FIG. 7 illustrates a known procedure for passing a cable 705 around the femur 150 using a cable passer 710. After the underlying hip surgery, the cable passer 710 is passed around the superior femur 150 usually from the posterior to the anterior. The free end of the cable 705 is inserted into the tip of the cable passer 710 until the free end exits the cable passer on the other end as shown. The cable passer 710 is then removed, leaving the cable 705 around the femur 150.

Figure 8:
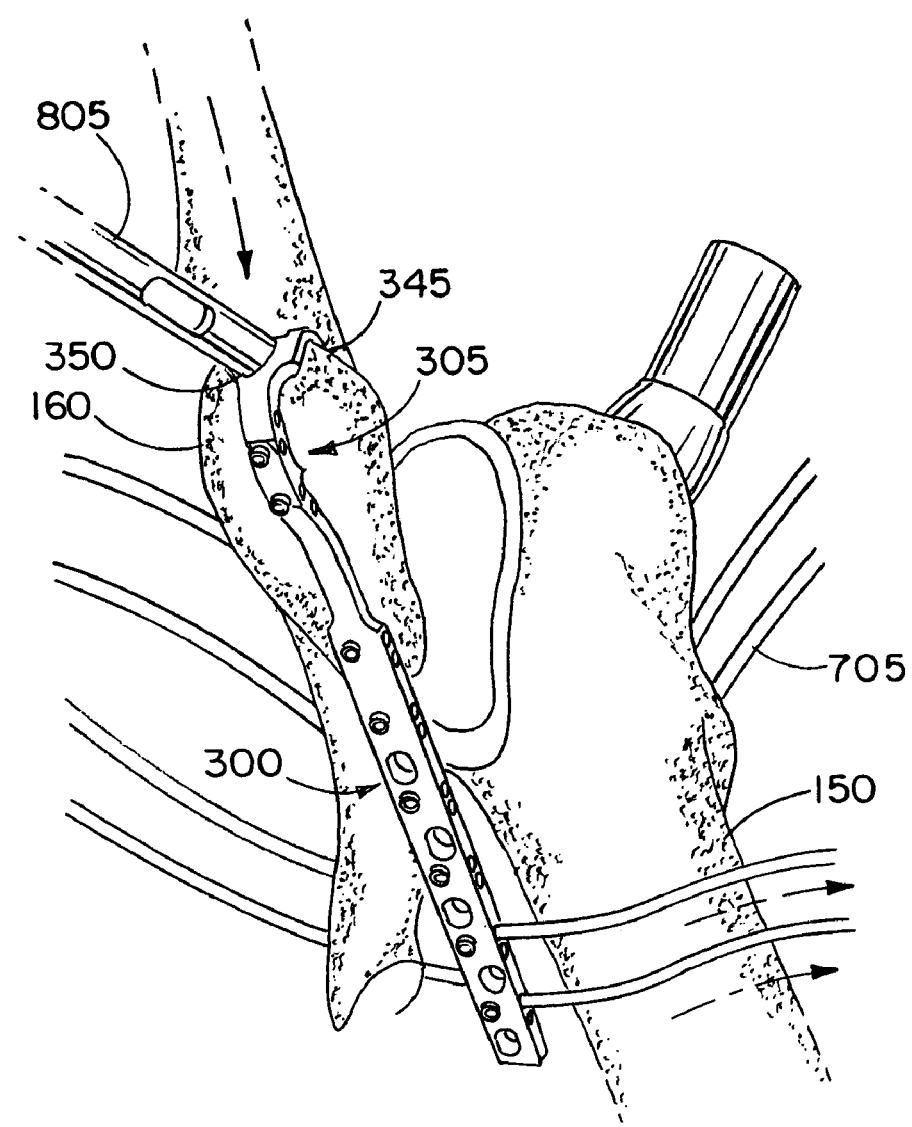

Referring to FIGS. 6 and 8, at step 605, a driver 805 is screwed onto the driver slot 350 of the connector 300. At step 610, the connector 300 is impacted onto the greater trochanter 160. The claws 345 at the extreme tip of the superior end 305 of the connector 300 should engage the superior portion of the trochanter 160.

Figure 9:
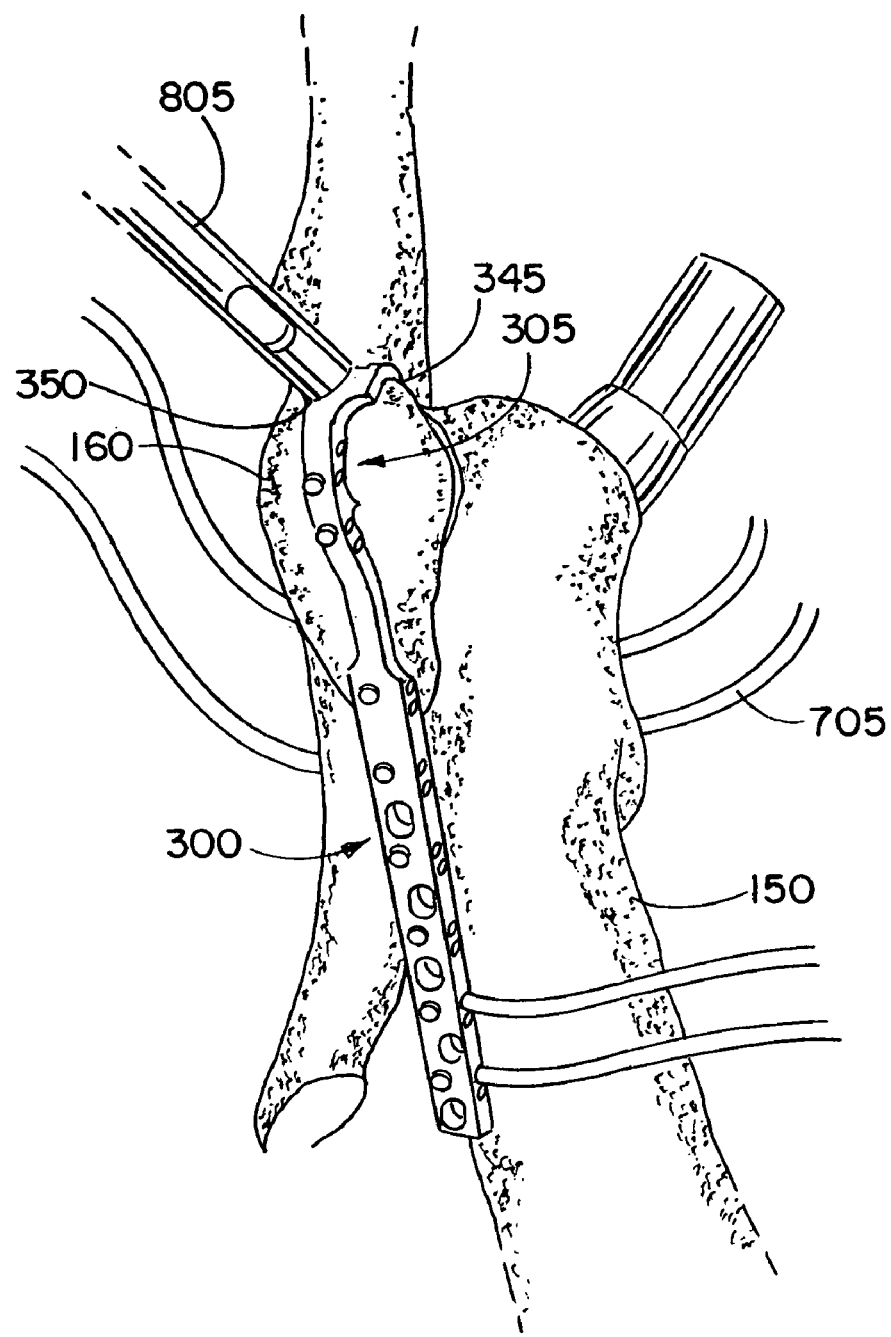

Referring next to FIGS. 6 and 9, at step 615, the driver 805 is used to advance the connector 300 and impacted greater trochanter 160 onto the femur 150.

Figure 10:
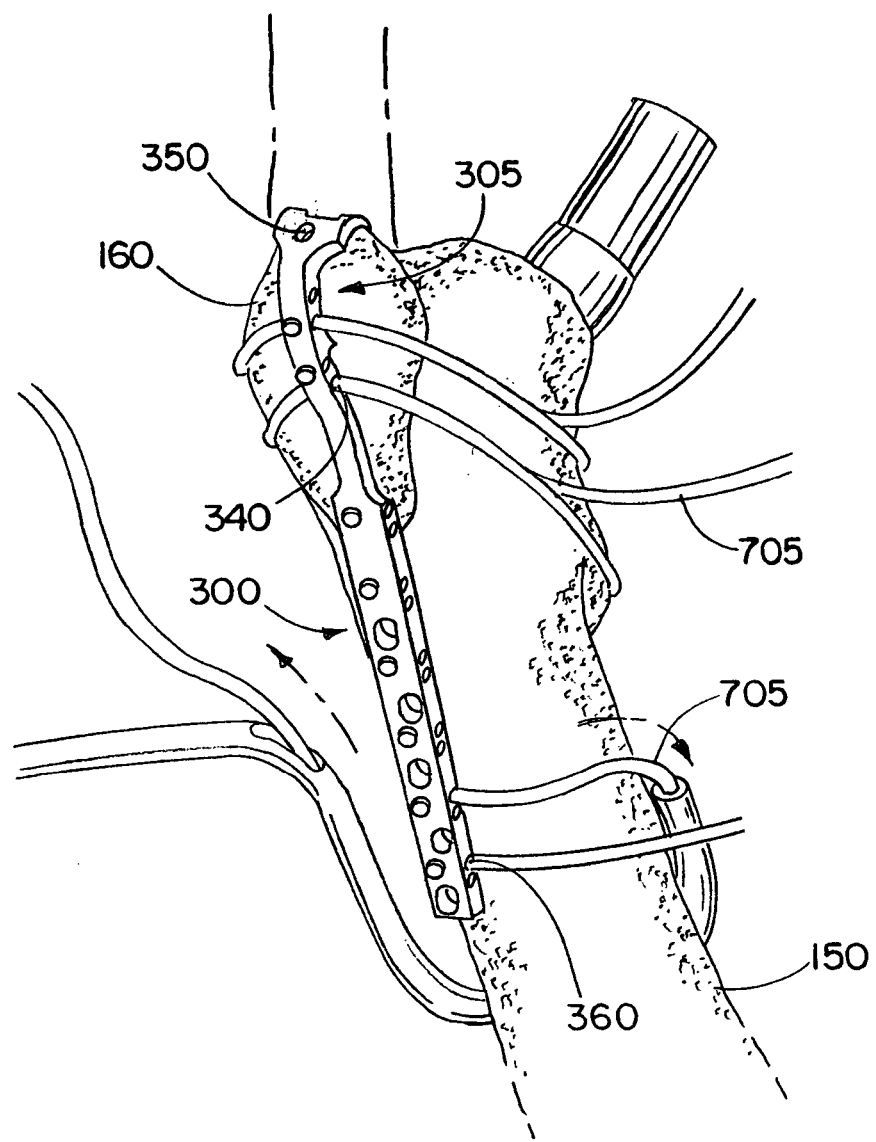

Referring next to FIGS. 6 and 10, at step 620, one or more cables 705 are passed around the femur 150 and through the apertures 340 and 360 of the connector 300.

Figure 11:
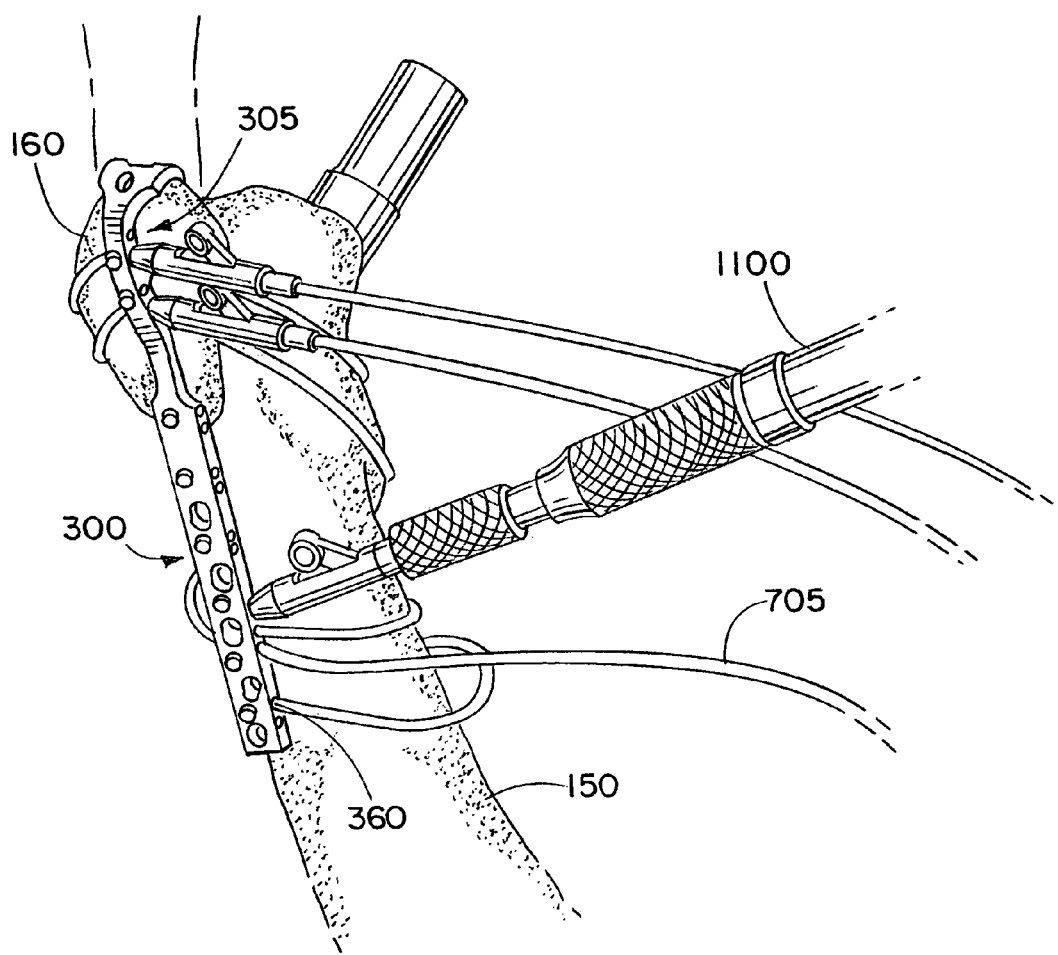

Referring next to FIGS. 6 and 11, at step 625, the cables 705 are tensioned using a tensioning tool 1100.

Figure 12:
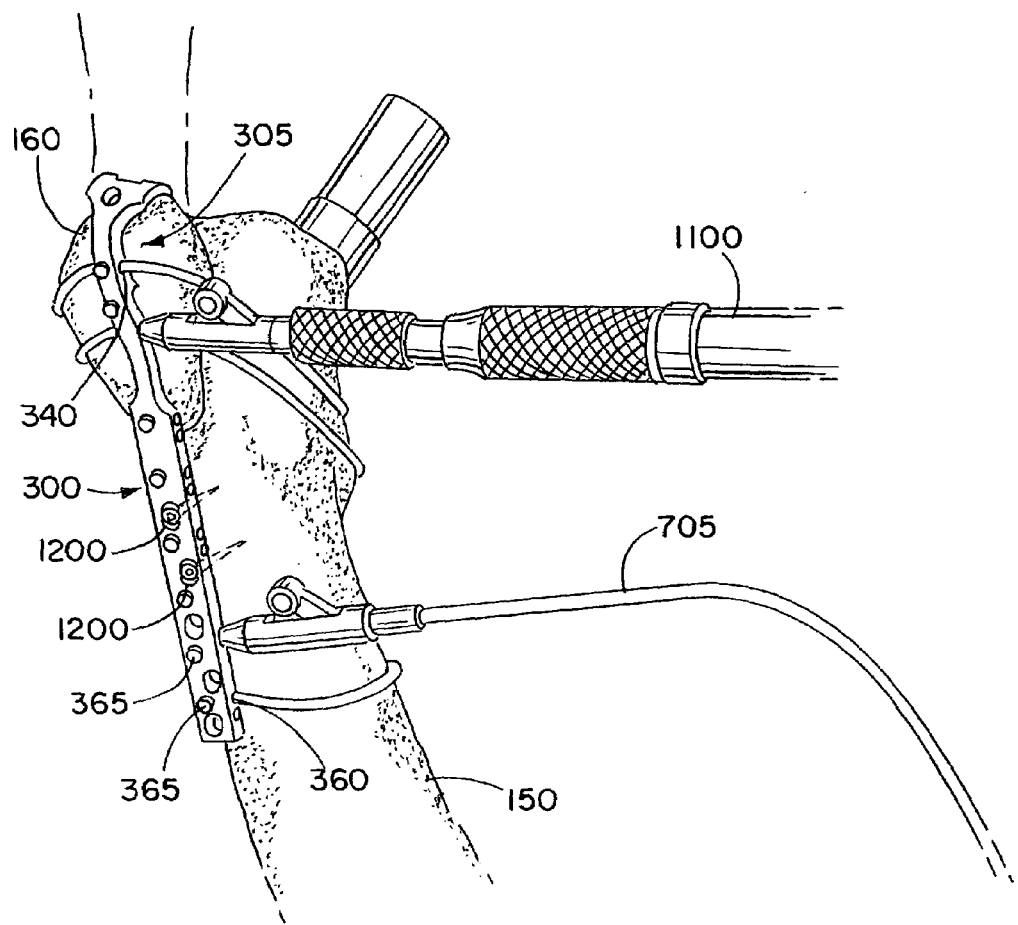
Figure 13:
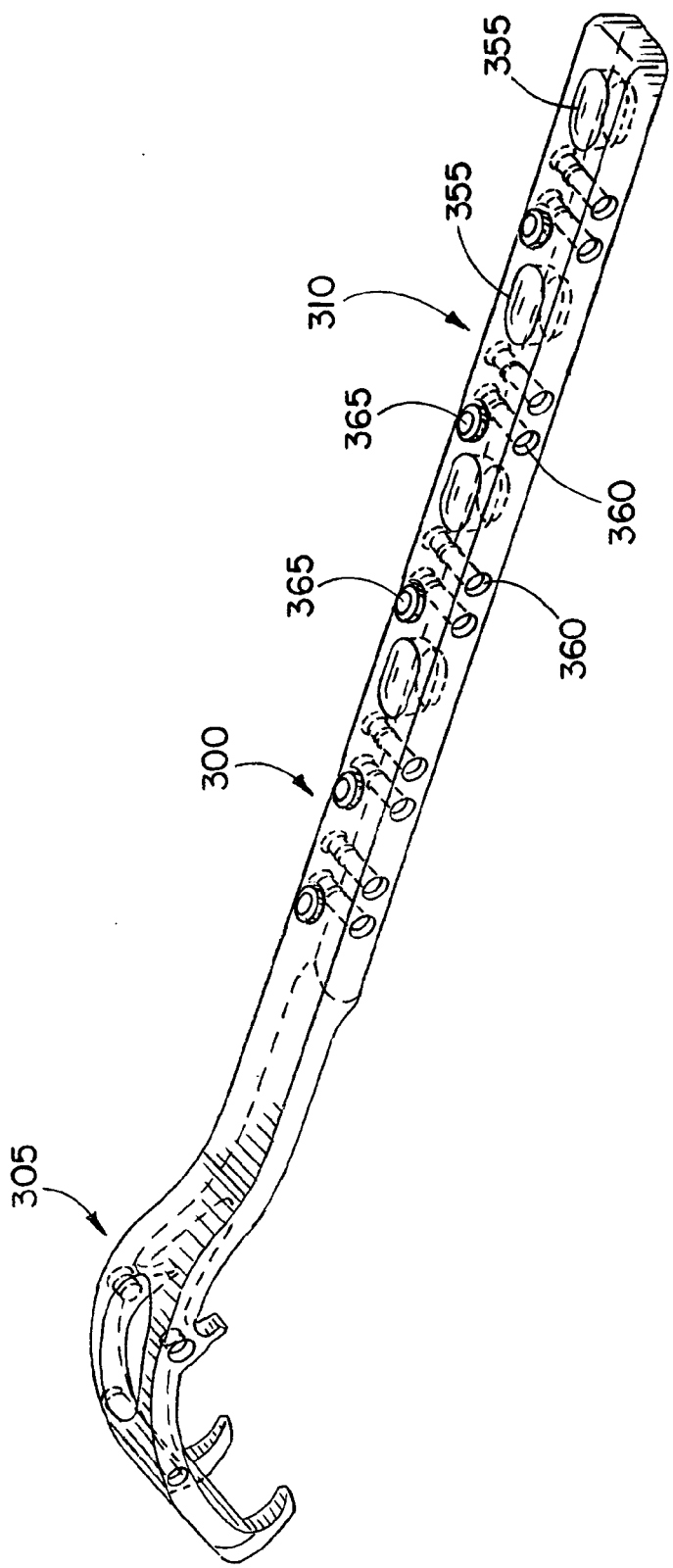
Figure 16:
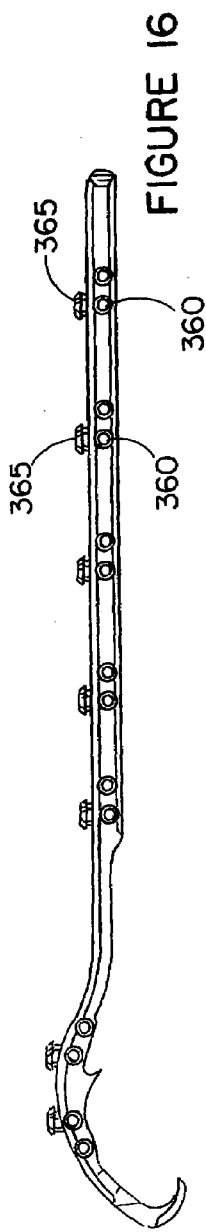
Figure 17:
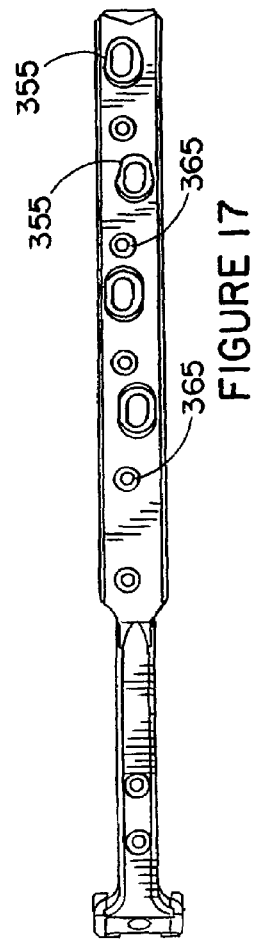
Figure 15:
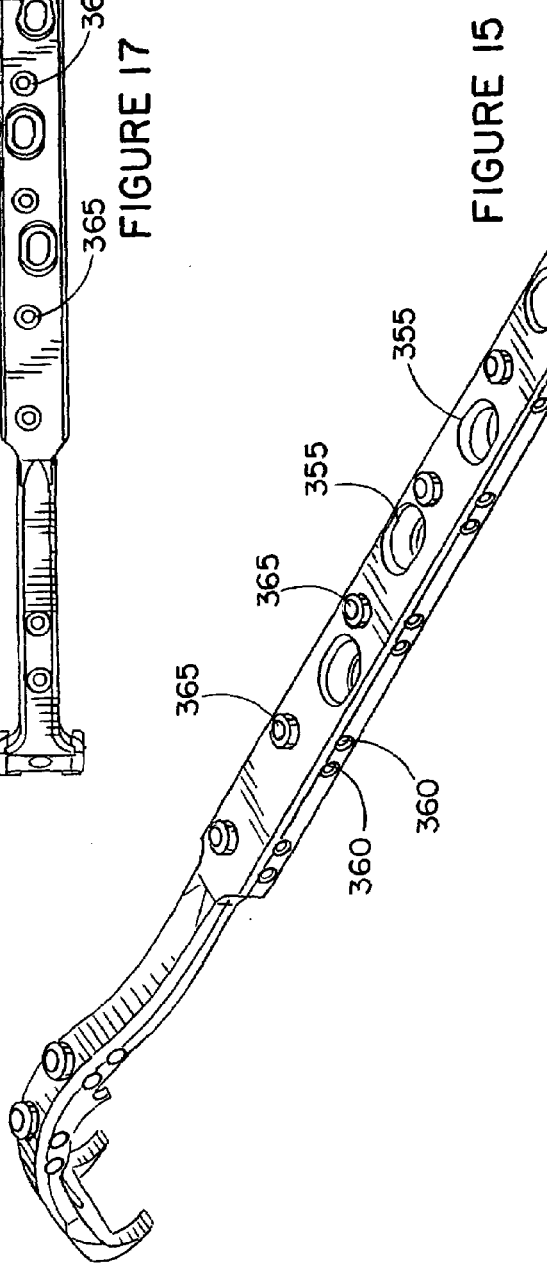

Referring next to FIGS. 6 and 12, at step 630, the bone screws 1200 are screwed through the bone screw slots 355 of the connector 300 and into the femur 150. Finally, step 635, the cables 705 are re-tensioned and locked-down with cable screws 365. Excess cable 705 is also cut away.

As will be recognized by those of ordinary skill, the present invention advantageously provides an improved technique for repairing periprosthetic fractures and/or re-attaching the greater trochanter 160 to the femur 150. Advantageously, slots 355 allow bone screws to be inserted into the femur 150 to provide a more durable connection, to provide torsional stability, to provide stability for bony fragments of periprosthetic fractures, and to provide more support for the greater trochanter 160 while it heals. The improved superior end 305 of the connector 300 provides an improved anatomically-designed bow that fits and cradles the greater trochanter 160. The superior end 305 allows cables 705 to be wrapped around that portion of the greater trochanter 160. Further, the improved inferior end 310 of the connector 300 allows the connector to be attached to the femur 150 with bone screws 1200 to provide a more durable connection, to provide more stability for the connector 300, and to provide more support for the greater trochanter 160 while it heals. In this regard, slots 355 are provided along the inferior end 310 of the connector 300.

Figure 18:
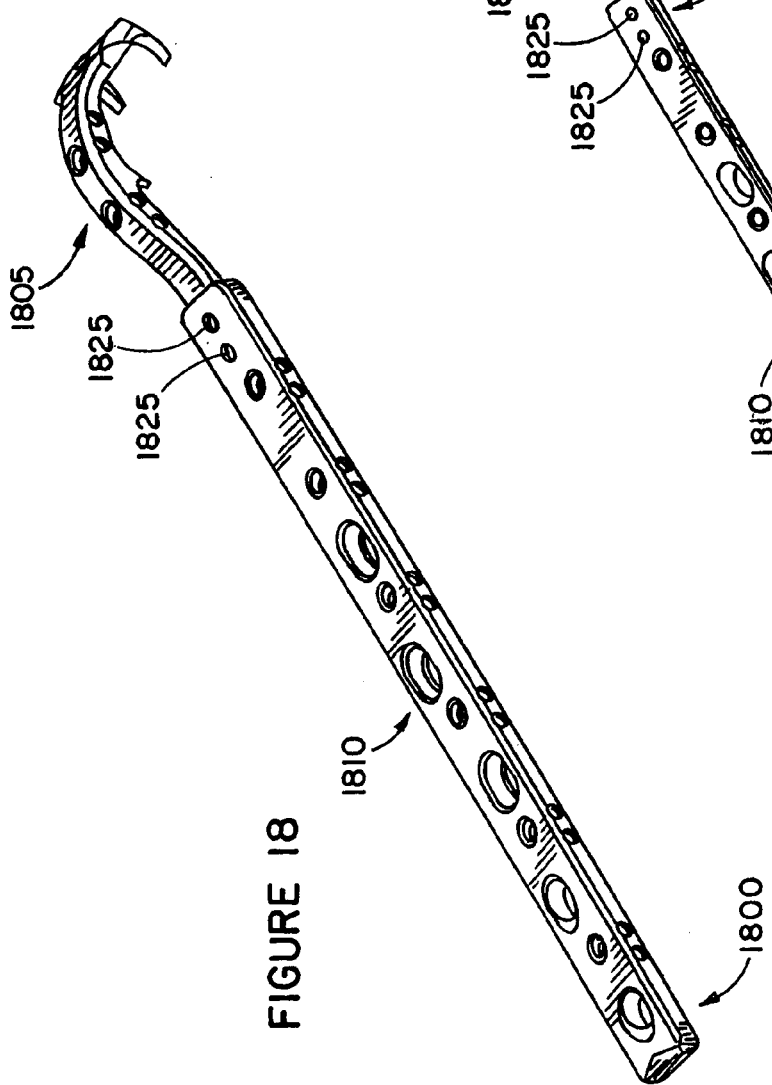
FIGS. 18–21 illustrate one embodiment of the present invention wherein the superior and inferior ends of the connector are modular.
Figure 19:
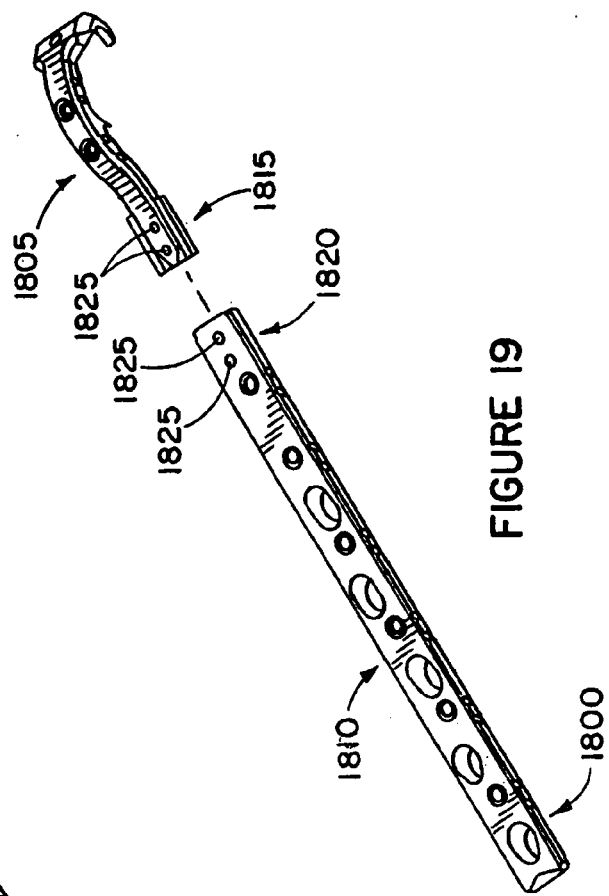
Figure 20:
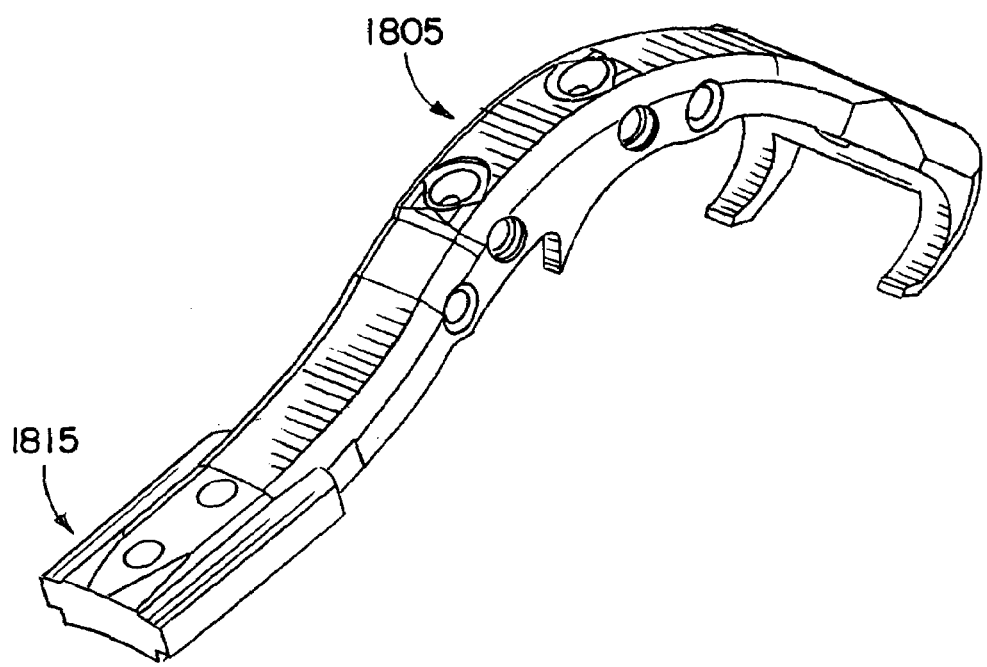
Figure 21:
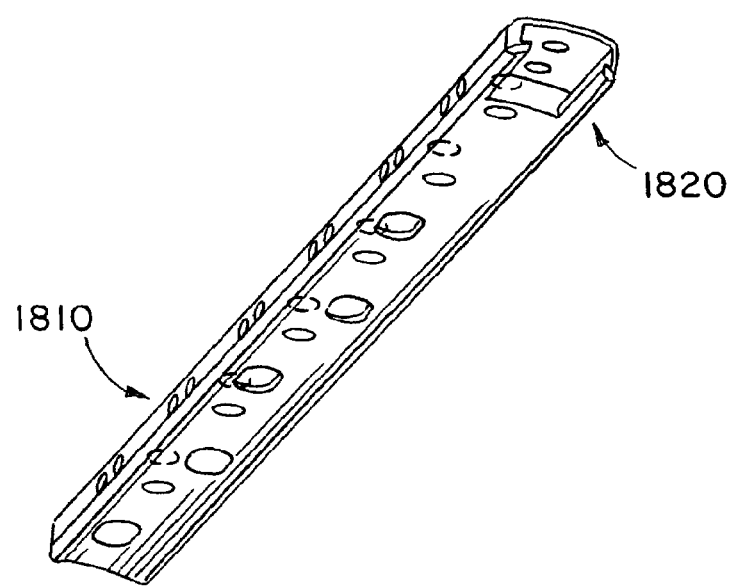

In another aspect of the present invention, the device includes a modularity feature. The modularity feature may be implemented, for example, by using a superior end and an inferior end of choice size to closely fit the patient's skeletal frame. FIGS. 18–21 illustrate one embodiment of a modular construction of the connector 1800 having a superior end 1805 and an inferior end 1810. FIG. 18 illustrates the superior and inferior ends 1805 and 1810 mated together and FIG. 19 illustrates detached superior and inferior ends 1805 and 1810. FIG. 20 illustrates the superior end 1805 with a first transition portion 1815 and FIG. 21 illustrates the inferior end 1810 with a second transition portion 1820. In the embodiments of FIGS. 20–21, the first and second transition portions 1815 and 1820 are a tongue and groove, respectively. The two ends 1805 and 1810 may be secured together using one or more screws though apertures 1825. It is clear, however, that one skilled in the art would be able to utilize a variety of methods for securing the two portions together. This modularity feature allows the apparatus to be fitted to femoral heads and femoral shafts of a variety of sizes and shapes without need for manufacture and inventory of an unreasonable number of differently sized models of this apparatus.

As used herein, the present invention may be used in a number of applications for repairing the human femur, including, but not limited to, total hip replacements, hip revisions, and repair of periprosthetic bone fractures and/or re-attaching the greater trochanter to the femur.

Although the preferred embodiment of this invention has been described hereinabove in some detail, it should be appreciated that a variety of embodiments will be readily available to persons utilizing the invention for a specific end use. The description of this invention is not intended to be limiting on this invention, but is merely illustrative of the preferred embodiment of this invention. Other products, apparatus and methods which incorporate modifications or changes to that which has been described herein are equally included within this application. Additional objects, features and advantages of the present invention will become apparent by referring to the above description of the invention in connection with the accompanying drawings.

We claim:

1. A connector for engaging along a femur that has an upper head end thereof with a prosthetic hip implant including a stem extending in the femur and a ball projecting from the femur head end, the connector comprising:
    an elongate lower portion for extending along the femur below the head end thereof;
    a substantially rigid body of the lower portion;
    a plurality of cable openings in the rigid lower portion body;
    a plurality of cables for being received in the cable openings to extend therethrough and about the femur;
    a plurality of apertures in the rigid lower portion body;
    a plurality of holding devices configured to be carried on the rigid lower portion body in the apertures for being advanced therein for securing the cables in the cable openings to secure the lower portion to the femur;
    an upper portion for greater trochanter reattachment to the femur upper head end the upper portion being integral with the lower portion;
    a body of the upper portion that has a predetermined arcuate configuration to cradle the greater trochanter; and
    at least one distal tip end of the arcuate upper portion body configured for biting into the greater trochanter so that the arcuate upper portion body securely cradles and grips the greater trochanter to avoid formation of screw through openings in the upper portion body and use of bone screws extending therethrough for securing the upper portion body to the greater trochanter and that may otherwise interfere with the prosthetic stem in the femur.

2. The connector of claim 1 wherein the lower portion body includes bone screw slots extending therethrough with the lower portion body having a longitudinal axis and the slots being elongated along the lower portion body axis to allow bone screws to be extended through the slots at various angles to the axis to avoid contacting the prosthetic stem in the femur.

3. The connector of claim 1 wherein the lower portion body includes bone screw through openings having tapered walls extending thereabout to provide a compression fit with bone screws received and tightened therein and for drawing the arcuate upper portion body tightly against the greater trochanter.

4. The connector of claim 1 wherein the upper portion body includes at least one cable retaining structure for receiving a cable extending therealong and about the greater trochanter and femur head end to secure the greater trochanter thereon.

5. The connector of claim 4 wherein the upper portion body includes a portion proximal to the lower portion that is narrower than the lower portion body, the cable retaining structure comprises a cable opening in the body portion, the body portion includes at least one aperture and a holding device configured to be carried on the narrow body portion in the aperture thereof.

6. The connector of claim 1 wherein the upper portion body includes a driver opening generally aligned with and opposite the distal tip end allowing a driver tool to engage therewith for driving the tip end into the greater trochanter from a remote position relative thereto.

7. A connector for reattaching a greater trochanter to a femur, the connector comprising:
- an elongate lower portion for extending along the femur;
- a plurality of bone screw openings in the elongate lower portion for fastening the lower portion along the femur;
- an arcuate upper portion configured for cradling the greater trochanter, the arcuate upper portion being integral with the elongate lower portion;
- cable retaining structure of the arcuate upper portion; and
- a cable for being received by the cable retaining structure to extend therealong and about the greater trochanter and femur for securing the arcuate upper portion thereto.

8. The connector of claim 7 wherein the lower and upper portions have a transverse width dimension with the arcuate upper portion being narrower in the width dimension than the elongate lower portion to minimize bending of the cable as the cable exits the retaining structure for extending about the femur and greater trochanter.

9. The connector of claim 8 wherein the cable retaining structure comprises a cable opening, and the narrow arcuate upper portion includes an aperture and a cable holding device carried in the aperture of the narrow arcuate upper portion for being advanced in the aperture to secure the cable in the cable opening.

10. The connector of claim 9 wherein the narrow arcuate upper portion includes an enlarged width end portion having a tooth for biting into the greater trochanter.

11. The connector of claim 7 wherein the arcuate upper portion includes a driver opening for allowing a driver tool to engage therewith and manipulate the arcuate upper portion from a remote position relative to the greater trochanter and femur.

* * * * *

UNITED STATES PATENT AND TRADEMARK OFFICE
CERTIFICATE OF CORRECTION

PATENT NO. : 7,207,993 B1  
APPLICATION NO. : 09/775891  
DATED : April 24, 2007  
INVENTOR(S) : Baldwin et al.

Page 1 of 1

It is certified that error appears in the above-identified patent and that said Letters Patent is hereby corrected as shown below:

First page, column 2 at "Attorney, Agent, or Firm" replace "Fltch" with --Fitch--.

Claim 1, column 6, line 29 after "end" insert --,--.

Signed and Sealed this

Twenty-sixth Day of June, 2007

JON W. DUDAS  
*Director of the United States Patent and Trademark Office*